US008358123B2

(12) United States Patent
Compain et al.

(10) Patent No.: US 8,358,123 B2
(45) Date of Patent: Jan. 22, 2013

(54) METHOD OF QUANTIFYING AN ANALYTE IN A LIQUID MEDIUM HAVING MAGNETIC PARTICLES BY APPLICATION OF A MAGNETIC FIELD TO THE LIQUID MEDIUM

(75) Inventors: Eric Compain, Simiane Collonge (FR); Catherine Rouzeau, Guyancourt (FR); Karine Bizet, Le Chesnay (FR)

(73) Assignee: Bertin Technologies, Montigny le Bretonneux (FR)

(*) Notice: Subject to any disclaimer, the term of this patent is extended or adjusted under 35 U.S.C. 154(b) by 337 days.

(21) Appl. No.: 12/670,175

(22) PCT Filed: Jul. 11, 2008

(86) PCT No.: PCT/FR2008/001023

§ 371 (c)(1), (2), (4) Date: Apr. 28, 2010

(87) PCT Pub. No.: WO2009/034271

PCT Pub. Date: Mar. 19, 2009

(65) Prior Publication Data

US 2010/0207606 A1 Aug. 19, 2010

(30) Foreign Application Priority Data

Jul. 27, 2007 (FR) ..................................... 07 05530

(51) Int. Cl.
*G01N 27/74* (2006.01)

(52) U.S. Cl. ...................................................... 324/204

(58) Field of Classification Search ........................ None
See application file for complete search history.

(56) References Cited

U.S. PATENT DOCUMENTS

| | | | | |
|---|---|---|---|---|
| 6,294,342 | B1 * | 9/2001 | Rohr et al. | 435/7.1 |
| 6,294,362 | B1 * | 9/2001 | Sharp et al. | 435/174 |
| 2006/0240572 | A1 | 10/2006 | Carron et al. | |
| 2007/0155024 | A1 * | 7/2007 | Miethe et al. | 436/524 |

FOREIGN PATENT DOCUMENTS

| | | | |
|---|---|---|---|
| WO | WO 01/14591 | A1 | 3/2001 |
| WO | WO 02/35205 | A2 | 5/2002 |
| WO | WO 03/044532 | A1 | 5/2003 |
| WO | WO 03/054523 | A2 | 7/2003 |
| WO | WO 2005/010543 | A1 | 2/2005 |
| WO | WO 2005/026681 | A2 | 3/2005 |

OTHER PUBLICATIONS

International Search Report for International Application No. PCT/FR2008/001023 mailed Jan. 28, 2009.

* cited by examiner

*Primary Examiner* — Vinh Nguyen
(74) *Attorney, Agent, or Firm* — Alston & Bird LLP

(57) ABSTRACT

Method of quantifying an analyte in a liquid medium by means of magnetic particles functionalized by specific ligands of the analyte being quantified, consisting in applying a magnetic field to a liquid medium for a time period several times shorter than that of the reaction between the analyte being quantified and the ligands of the magnetic particles, in measuring the optical density of the liquid medium after applying the magnetic field, in repeating this cycle of applying the magnetic field and of measuring the optical density several times over the duration of the reaction between the analyte and the ligands, in calculating, by extrapolation, a limiting value for the optical density for an infinite magnetic field application time and in deducing therefrom the concentration of the analyte in the liquid medium.

13 Claims, 3 Drawing Sheets

METHOD OF QUANTIFYING AN ANALYTE IN A LIQUID MEDIUM HAVING MAGNETIC PARTICLES BY APPLICATION OF A MAGNETIC FIELD TO THE LIQUID MEDIUM

CROSS REFERENCE TO RELATED APPLICATIONS

This application is a national stage application filed under 35 U.S.C. 371 of International Application No. PCT/FR2008/001023, filed Jul. 11, 2008, which claims priority from French Application No. 07 05530, filed Jul. 27, 2007.

FIELD AND BACKGROUND OF THE INVENTION

The invention relates to a method of quantifying at least one analyte in a liquid medium, this method including a reaction of the analyte with ligands grafted onto magnetic particles contained in the liquid medium.

A quantifying method of this type is known from the document WO 03/044532, which consists in applying a magnetic field to a liquid medium containing the analyte being quantified and magnetic particles functionalized at the surface with specific ligands of the analyte being quantified. The magnetic field has an intensity sufficient to cause the formation of chains or clusters of magnetic particles, and the application thereof to the liquid medium is maintained for a sufficient period of time for the analyte to be coupled or associated with the ligands of the magnetic particles, after which the field is cancelled, thereby causing the separation of those magnetic particles the ligands of which have not reacted with the analyte being quantified. The presence of the analyte in the liquid medium can be determined by direct observation under a microscope or preferably by measuring a parameter such as the optical density of the liquid medium. The concentration of same can also be determined by measuring the variation of the optical density of the liquid medium, between a moment t0, which corresponds to the start of the magnetic field application, and a moment t1, which follows the cancellation of the magnetic field at the end of the reaction between the analyte and the ligands.

The value of the variation in optical density between t0 and t1 is compared with calibration curves or values obtained with known concentrations of the analyte being quantified.

This method has the advantage of having a detection limit which is lower than that of conventional agglutination methods carried out in the absence of a magnetic field.

SUMMARY OF THE INVENTION

The object of this invention, in particular, are modifications in this method, which enable the detection limit thereof to be lowered further and the strength thereof to be improved.

To that end, it proposes a method of quantifying an analyte in a liquid medium, which consists in placing magnetic particles in this medium, which have been functionalized by specific ligands of the analyte being quantified, in causing a magnetic field to act on the liquid medium, thereby enabling adhesion of the magnetic particles and the formation of clusters of magnetic particles, and in determining the presence and concentration of the analyte from the variation of a parameter such as the optical density of the liquid medium, for example, the value of this parameter being measured prior to application of the magnetic field, characterised in that it includes repeated cycles of applying the magnetic field to the liquid medium and of measuring the parameter after each application of the magnetic field, the magnetic field application period during each cycle being shorter than that of the reaction between the analyte being quantified and the ligands of the magnetic particles, the method likewise consisting in calculating, on the basis of the aforesaid measurements, a limiting value for the variation in the parameter for an infinite magnetic field application time, and in deducing therefrom the concentration of the analyte in the liquid medium.

In general, the invention enables the signal-to-noise ratio of the measurements to be improved and the detection limit to be lowered by a factor equal to at least 5.

The method according to the invention includes n repetitions of the cycle of applying the magnetic field and of measuring the parameter over the duration of the reaction between the analyte and the ligands, n being between 2 and 100, and preferably between 5 and 60.

The total duration of the magnetic field application over the n cycles is shorter than or substantially equal to the duration of the reaction between the ligands and the analyte.

The magnetic field application time for one cycle is between 1 second and 1 minute, and is preferably between 10 seconds and 50 seconds.

The measurement of the aforesaid parameter value is preferably taken at the end of each cycle, during a return to equilibrium in the liquid medium, i.e., after at least partial dispersion of the clusters of magnetic particles.

The number of cycles n is determined such that the total magnetic field application time is equal to p times the time constant of the variation in the measured parameter, this variation being of the exponential type.

P is preferably equal to 2.

More generally speaking, p is between 0.5 and 5.

According to another characteristic of the invention, the method likewise consists in calculating the variation in the measured parameter, at the end of each cycle, for a magnetic field application time accumulated from the first cycle carried out, and in calculating, by extrapolation, a limiting value that the calculated value approaches for an infinite magnetic field application time.

The calculations of the variation in the parameter are advantageously made in real time at the end of each cycle.

Alternatively, when possible, these calculations can be made following the end of the reaction between the analyte and the ligands. The calculations of the variations in the parameter over the time periods accumulated since the first cycle and of the variation in the parameter for an infinite magnetic field application time are coupled, and, when calculating the variations in the parameter over the accumulated magnetic field application times, account is taken of the variations in time constants due to the reduction in mobility of the liquid medium.

This method likewise advantageously consists in identifying and filtering parasitic phenomena which have an influence on the measured parameter. In order to accomplish this, the method consists in mathematically breaking down the temporal evolution of the measured parameter in a functions base having time constants representative of the kinetics of the system and in retaining only those functions having time constants characteristic of the specific adhesion of the ligands and of the analyte being quantified. This treatment enables the measurements of the parameter to be filtered and the selectivity of the method to be improved.

BRIEF DESCRIPTION OF THE DRAWINGS

The invention will be better understood and other characteristics, details and advantages thereof will become more apparent upon reading the following description, which is given for illustrative purposes with reference to the appended drawings, in which.

DETAILED DESCRIPTION OF THE INVENTION

As already indicated, this method is generally of the same type as that described in the document WO 03/044532, and uses colloidal particles (having dimensions preferably between 100 and 1000 nm) of a superparamagnetic material, which can quickly organize into chains or clusters of particles, under the effect of a magnetic field, and quickly separate at the end of the magnetic field application.

These particles are functionalized at the surface with specific ligands of the analyte being quantified, the functionalisation of the magnetic particles by the ligands being carried out conventionally, as described, for example, in the document WO 03/044532.

Figure 1:
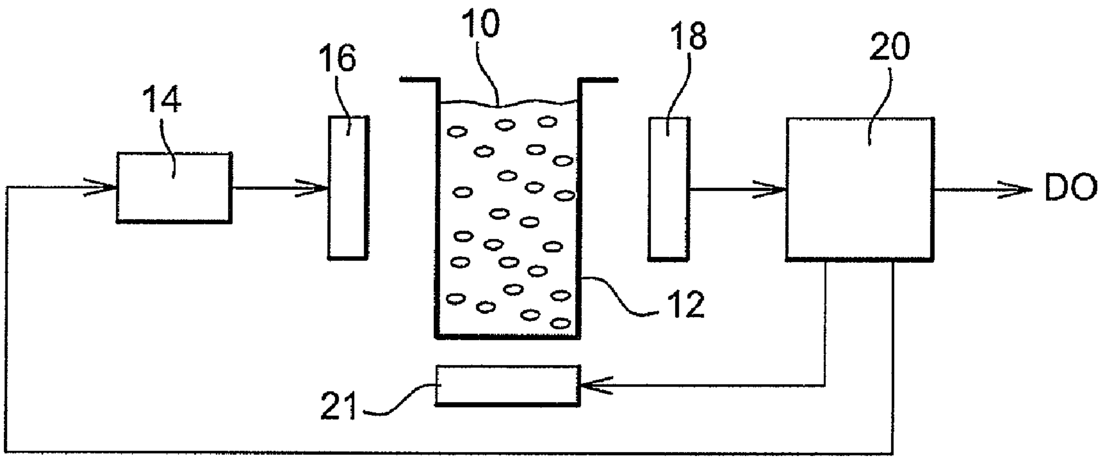
FIG. 1 is a schematic representation of a quantification device according to the invention.
Figure 2:
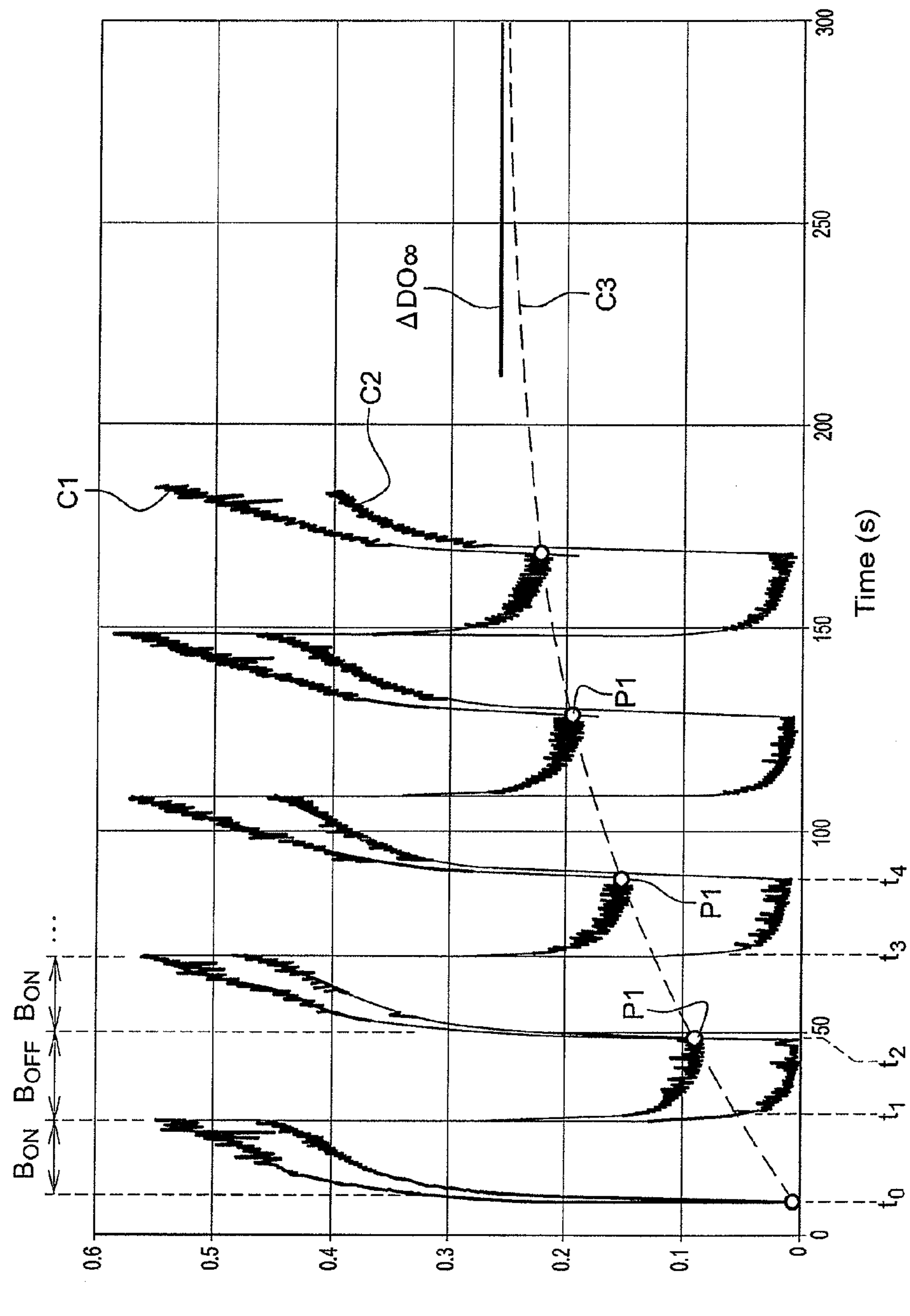
FIG. 2 is a graph showing the principal steps of the quantification method according to the invention.

A predetermined volume of a solution 10 of functionalized magnetic colloidal particles is placed together with an analyte sample being quantified in an appropriate container 12 made of a transparent plastic material. A magnetic field having an intensity of approximately 10 to 40 mT is applied to the container 12, e.g., by placing it between two permanent magnets or on an electromagnet 21 or between two electromagnets, and the optical density of the liquid medium 10 is measured by using a light source 14, e.g., such as a laser generator associated with an appropriate optic 16, in order to illuminate the container 12, and a photodetector 18, e.g., such as a photodiode, or a set of photodetectors, e.g., such as a CCD or CMOS camera, the output of which is connected to an input of information processing means 20 which control the light source 14 and the photodetectors 18 and which supply an output signal DO of the optical density of the liquid medium, the time-dependent variation of which is shown by the graph of FIG. 2. Means 20 likewise enable control of the means of applying and cutting off the magnetic field (e.g., the electromagnet 21), in order to synchronize the measurements with the presence of the magnetic field within the liquid medium 10.

According to the invention, the magnetic field is applied cyclically to the liquid medium 10 containing the sample being quantified, each cycle including two phases and having a duration which is shorter than the reaction time between the analyte and the ligands attached to the magnetic particles. The first phase is characterised by the application of the magnetic field ($B_{ON}$ in FIG. 2) and has a duration which is longer than the magnetic cluster formation time. The second phase is characterised by a zero magnetic field ($B_{OFF}$ in FIG. 2), and has a duration which is at least equal to or longer than the dispersion time for the particle clusters, and, if possible, for the non-specific adhesions between the particles, and which is shorter than the time constant for the dissociation of the specific adhesions between the ligands and the analyte. The optical density of the liquid medium is measured at the start of each cycle and at the end of each cycle. The optical density is preferably sampled over the entire duration of the process, the sampling period being shorter in comparison with the cycle time and characteristic time constants of the system. It is typically between 10 ms and 1 second. The magnetic field application time in each cycle is determined so that these cycles can be repeated n times over the duration of the reaction between the ligands and the analyte being quantified. This parameter n is generally between 2 and 100, preferably between 5 and 60, and, in actual practice, it can be equal to approximately 20 or 30. For reasons of simplification and legibility of the drawings, it is equal to 4 in FIGS. 2 and 3.

The magnetic field application time during each cycle is generally between one second and one minute, and preferably between 10 seconds and 50 seconds, based on the total reaction time between the ligands and analytes.

In the graph of FIG. 2, curve C1 represents the variation in optical density of the liquid medium, measured in number of decades of light attenuation, in relation to the time measured in seconds, in the case of a liquid medium containing a high concentration of the analyte being quantified, curve C2 representing the variation in optical density of the liquid medium containing a very low concentration of the analyte being quantified.

A time t0, the optical density of the liquid medium is measured once in the absence of a magnetic field, and then the magnetic field is applied (phase $B_{ON}$). The optical density of the liquid medium increases very rapidly, and then the magnetic field is cut off at time t1, which results in a very rapid decrease in the optical density of the liquid medium (phase $B_{OFF}$). The time interval t0-t1 is approximately 20 seconds here. The optical density of the liquid medium is measured again at time t2, after a partial return to equilibrium in the liquid medium, the interval t1-t2 being approximately 20 seconds, and then the magnetic field is once again applied for a period of approximately 20 seconds and is then cut off at moment t3, the optical density of the liquid medium being measured again at moment t4, after a return to equilibrium, and so on and so forth. The cycles for applying and cutting off the magnetic field and of measuring the optical density of the liquid medium are repeated until the reaction between the ligands and the analyte being quantified has advanced sufficiently, the duration of this reaction possibly being of the order of several minutes. The acquisitions of the optical parameter values at the end of each cycle are shown by points P1. These points make it possible to calculate an exponential-type curve C3 by extrapolation, and to extrapolate a limiting value $\Delta DO\infty$ which is that which the parameter would reach after an infinite number of cycles.

The values P1 are optical density values typically averaged over 5 seconds. When, as in the aforesaid document WO 03/044532, the optical density is measured once prior to applying the magnetic field and once after applying the field, the total acquisition time for the measurement is approximately 10 seconds. In addition, the process remains long because it is necessary to wait for the liquid medium to become completely stabilized after cutting off the magnetic field.

When, in accordance with the invention, these measurements are repeated 30 times to acquire the values P1, the total acquisition time is approximately 300 seconds, which enables a factor equal to $\sqrt{30}$, or approximately 5 to 6 to be gained over the signal-to-noise ratio of the value $\Delta DO\infty$. In this case, the noise is, among other things, optical noise, which is due to the agitation of the particles in the liquid medium, which enter and leave the measurement volume, and the noise of the measurement acquisition chain including the light source 14, the photodetectors 18 and the signal digitization and processing means. Furthermore, the extrapolation of the limiting value enables the duration of the process to be reduced while at the same time limiting the influence of the variations in time constants due to temperature, for example.

This improvement in the signal-to-noise ratio enables the detection limit of the quantification method to be lowered significantly.

Figure 3:
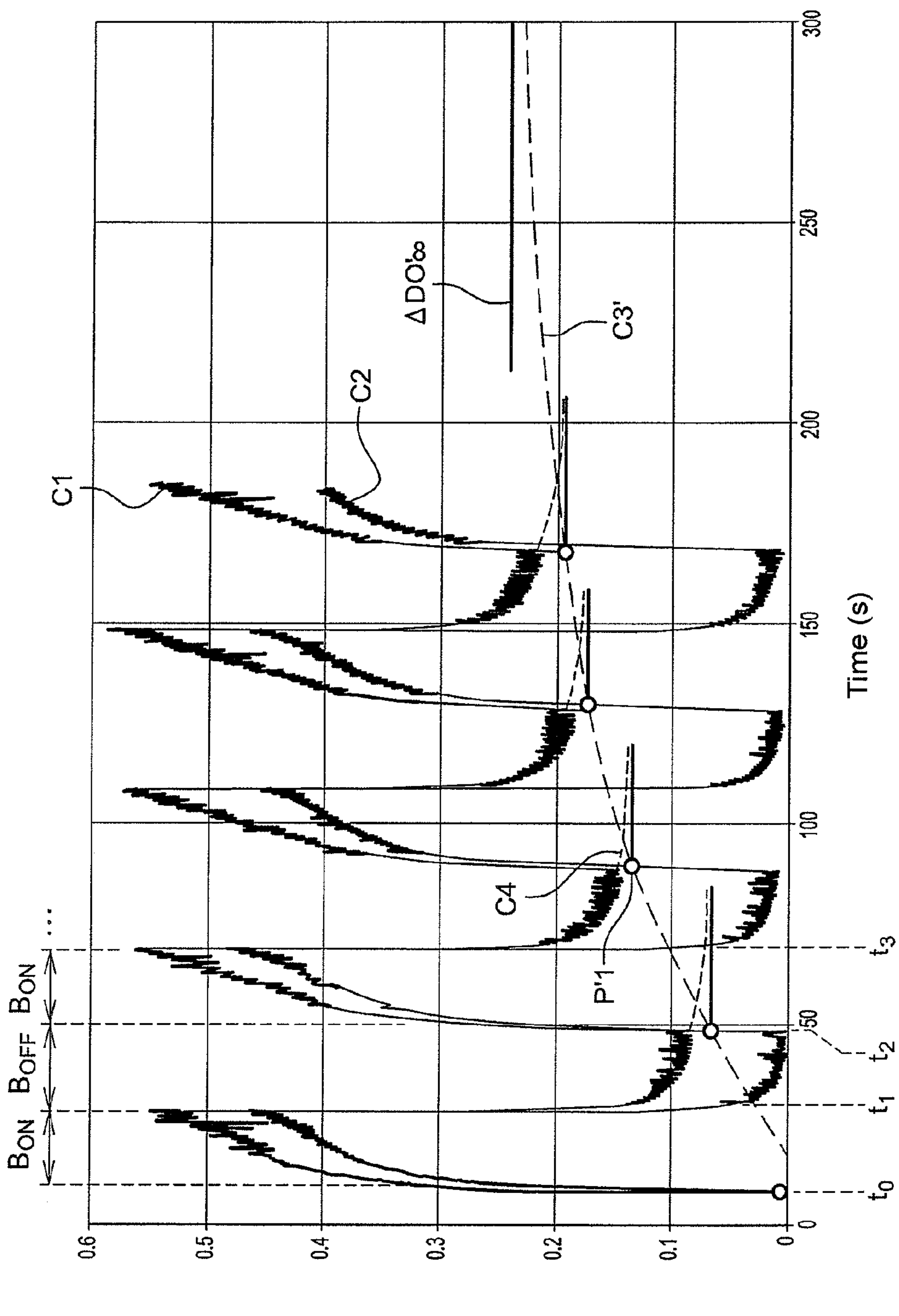
FIG. 3 is a graph showing the principal steps of an alternative of the quantification method according to the invention.

This detection limit can be further lowered by using the alternative of the method shown in FIG. 3. This alternative takes account of slow drift phenomena such as sedimentation, the thermal drift of the measurement means and of the non-specific adhesions, i.e., the colloidal magnetic particles which adhered temporarily without any reaction between the ligands that they contain and the analyte being quantified.

In order to accomplish this, at the end of each cycle of applying the magnetic field and of measuring the optical density, a calculation is made, by extrapolation (by means of curve C4) of the limiting value P'1 for the decrease in optical density of the liquid medium following a field application which has accumulated since the start of the first cycle and after a return to equilibrium of the liquid medium. The extrapolation enables optimization of the signal-to-noise ratio, by using more measurements, and a reduction in the cycle time.

Following n cycles of applying the magnetic field and of measuring the optical density, values P'1 are calculated by extrapolation, and a curve C'3, which passes through points P'1, and a limiting value ΔDO'∞ for the variation in optical density due to specific adhesions, i.e., to the reactions between the ligands of the magnetic particles and the analyte being quantified are calculated by filtering the parasitic phenomena.

The calculation takes account of the previously calculated n values P'1 for the variation in measured optical density, for cumulative magnetic field application times, and the extrapolation is made for an infinite magnetic field application time. The filtering consists in retaining, in the optical density increase terms, only those for which the time constants correspond to specific adhesions. This makes it possible to eliminate a certain number of parasitic phenomena which were identified during the calibration operations and the time constants of which do not correspond to the ligands/analyte being quantified reaction. In particular, the non-specific adhesions correspond to weaker bonding forces and have more rapid dissociation constants. The time constants for the ligands/analyte being quantified reaction are calibrated ahead of time in order to optimise selectivity.

The number of cycles of applying the magnetic field and of measuring optical density is preferably chosen such that the total magnetic field application time is equal to a few times the time constant of the optical density variation curve due to specific adhesions, the total magnetic field application time ideally being equal to twice this time constant.

The majority of the calculations can thus be carried out in real time, over the duration of the reaction between the ligands and the analyte being quantified, and post-processing is limited to calculating the limiting value ΔDO'∞ for the variation in optical density due to specific adhesions.

Alternatively, and if the calculating capacity of the processing means 20 and the total measurement time so permit, the calculations can be carried out entirely at the end of the quantifying reaction. In this case, the computational algorithms for the limiting values P'1 of the variation in optical density measured at the end of each cycle and of the variation in optical density ΔDO'∞ due to specific adhesions are paired such that, in calculating the values P'1, they are capable of taking account of the changes in time constants due to the reduction in mobility of the liquid medium, this phenomenon being measureable from the variation in optical density due to specific adhesions.

Generally speaking, the invention is applicable to the detection of antigens of any type by means of natural or synthetic ligands of any type. It enables the detection limit of an analyte to be lowered by a factor equal to at least five.

For example, in the case of detecting a recombinant factor of the botulinum toxin using monoclonal antibodies, the invention enabled the detection limit to be lowered by $2\cdot10^{-11}$ to $4\cdot10^{-12}$ mole of analyte per litre of liquid medium.

The invention claimed is:

1. Method of quantifying an analyte in a liquid medium, comprising the steps of:

placing magnetic particles in a liquid medium, wherein the magnetic particles have been functionalized by specific ligands of the analyte being quantified;

causing a magnetic field to act on the liquid medium, thereby enabling adhesion of the magnetic particles and the formation of clusters of magnetic particles, determining the presence and concentration of the analyte from the variation of a parameter, the value of this parameter being measured prior to application of the magnetic field, wherein the method includes repeated cycles of applying the magnetic field to the liquid medium and of measuring the parameter after each application of the magnetic field, and wherein the magnetic field application period during each cycle being shorter than that of the reaction between the analyte being quantified and the ligands of the magnetic particles, calculating, on the basis of the aforesaid measurements, a limiting value for the variation in the parameter for an infinite magnetic field application time, and deducing therefrom the concentration of the analyte in the liquid medium.

2. Method of claim 1, wherein the method includes n cycles of applying the magnetic field and of measuring the parameter over the duration of the reaction between the analyte and the ligands, n being between 2 and 100.

3. Method of claim 2, wherein n is between 5 and 60.

4. Method as claimed in claim 1, wherein the magnetic field application time during one cycle is between 1 second and 1 minute.

5. Method of claim 4, wherein the magnetic field application time during one cycle is between 10 seconds and 50 seconds.

6. Method as claimed in claim 1, wherein the method further includes measuring the parameter at the end of each cycle, after a return to equilibrium in the liquid medium.

7. Method as claimed in claim 1, wherein the method further includes determining the number of cycles n such that total magnetic field application time is equal to p times the time constant of the variation in the parameter measured, this variation being of the exponential type.

8. Method of claim 7, wherein p is equal to 2.

9. Method as claimed in claim 1, wherein the method further includes calculating the variation in the measured parameter, at the end of each cycle, for a magnetic field application time accumulated from a first cycle carried out, and in calculating, by extrapolation, a limiting value that the calculated value approaches for an infinite magnetic field application time.

10. Method of claim 9, wherein the calculations of the variation in the parameter are carried out at the end of the reaction between the analyte and the ligands, in that the calculations of the variations in the parameter over the time periods accumulated from the first cycle and of the variation in the parameter for an infinite magnetic field application time are paired, and in that, in calculating the variations in the of the parameter over the cumulative magnetic field application times, account is take of the reduction in the mobility of the liquid medium.

11. Method as claimed in claim 1, wherein that the calculations of the variation in the parameter are carried out in real time, at the end of each cycle.

12. Method as claimed in claim 1, wherein the method further includes identifying and in eliminating by filtration the parasitic phenomena influencing the measured parameter, and, in order to accomplish this, in measuring the time constants for the reaction of the ligands and the analyte, for high analyte concentrations, in breaking down the temporal evolution of the measured values in a functions base having different time constants and in retaining only those components of the measured values which have time constants corresponding to those of the ligands-analyte reaction.

13. Method as claimed in claim 1, wherein the parameter is the optical density of the liquid medium.

* * * * *

UNITED STATES PATENT AND TRADEMARK OFFICE

CERTIFICATE OF CORRECTION

PATENT NO. : 8,358,123 B2
APPLICATION NO. : 12/670175
DATED : January 22, 2013
INVENTOR(S) : Compain et al.

It is certified that error appears in the above-identified patent and that said Letters Patent is hereby corrected as shown below:

In the Specifications

Column 7,
Line 4, "wherein that the" should read --wherein the--.

Signed and Sealed this
Thirteenth Day of August, 2013

Teresa Stanek Rea
*Acting Director of the United States Patent and Trademark Office*